US00PP23503P3

(12) United States Plant Patent
Drane et al.

(10) Patent No.: US PP23,503 P3
(45) Date of Patent: Mar. 26, 2013

(54) ***CORDYLINE* PLANT NAMED 'MYSTIC JOY'**

(50) Latin Name: *Cordyline brasiliensis*
Varietal Denomination: Mystic Joy

(76) Inventors: Walter John Drane, Ningi (AU); Doreen Joy Drane, Ningi (AU)

( * ) Notice: Subject to any disclaimer, the term of this patent is extended or adjusted under 35 U.S.C. 154(b) by 0 days.

(21) Appl. No.: 13/199,125

(22) Filed: Aug. 19, 2011

(65) Prior Publication Data

US 2013/0047307 P1 Feb. 21, 2013

(51) Int. Cl.
*A01H 5/00* (2006.01)

(52) U.S. Cl. ..... Plt./383

(58) Field of Classification Search ..... Plt./383
See application file for complete search history.

*Primary Examiner* — Howard Locker
(74) *Attorney, Agent, or Firm* — Cassandra Bright

(57) ABSTRACT

A new and distinct *Cordyline* cultivar named 'Mystic Joy' is disclosed, characterized by very moderately variegated foliage of green with a thin red-purple margin, moderate leaf production along the stem, and medium sized foliage. The new variety is a *Cordyline brasiliensis*, normally used for ornamental garden or container plantings.

2 Drawing Sheets

Latin name of the genus and species: *Cordyline brasiliensis*.

Variety denomination: 'MYSTIC JOY'.

BACKGROUND OF THE INVENTION

The new variety originated as a naturally occurring, whole plant mutation from the parent variety *Cordyline brasiliensis* 'Pink Joy', U.S. Plant Pat. No. 19,959. The color variation was discovered at a commercial nursery in Ningi, Queensland, Australia by the inventors, Walter John Drane and Doreen Joy Drane in 2006.

Asexual reproduction of the new cultivar 'Mystic Joy' was first performed in Ninji, Queensland Australia by vegetative cuttings, during December of 2006. Multiple generations have since been produced by vegetative cuttings, establishing the distinctive foliage characteristics of 'Mystic Joy' are stable and reproduced true to type through multiple generations.

SUMMARY OF THE INVENTION

The cultivar 'Mystic Joy' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Mystic Joy' These characteristics in combination distinguish 'Mystic Joy' as a new and distinct *Cordyline* cultivar:

1. Moderately variegated foliage of green with a thin red-purple margin.
2. Moderate leaf production along stem.
3. Medium foliage size between 'Glauca' and 'Pink Joy'.

COMPARISON TO THE PARENT VARIETY

Plants of the new cultivar 'Mystic Joy' are similar to plants of the parent variety, *Cordyline brasiliensis* 'Pink Joy' U.S. Plant Pat. No. 19,959, in most horticultural characteristics.

However, foliage of the new cultivar 'Mystic Joy' has a darker, thinner coloration along the margin. Additionally 'Mystic Joy' grows faster, produces larger leaves, less leaves per stem, and a broader plant form. 'Mystic Joy' has also demonstrated greater resistance to root rot disease, and a lower temperature tolerance than 'Pink Joy'.

COMMERCIAL COMPARISON

Plants of 'Mystic Joy' can also be compared to *Cordyline brasiliensis* 'Glauca', unpatented. Plants of the two varieties are similar in most horticultural characteristics. However, plants of 'Mystic Joy' produce small foliage. Additionally, foliage is 'Glauca' is solid green, whereas 'Mystic Joy' has moderately variegated foliage.

BRIEF DESCRIPTION OF THE PHOTOGRAPHS

Figure 1:
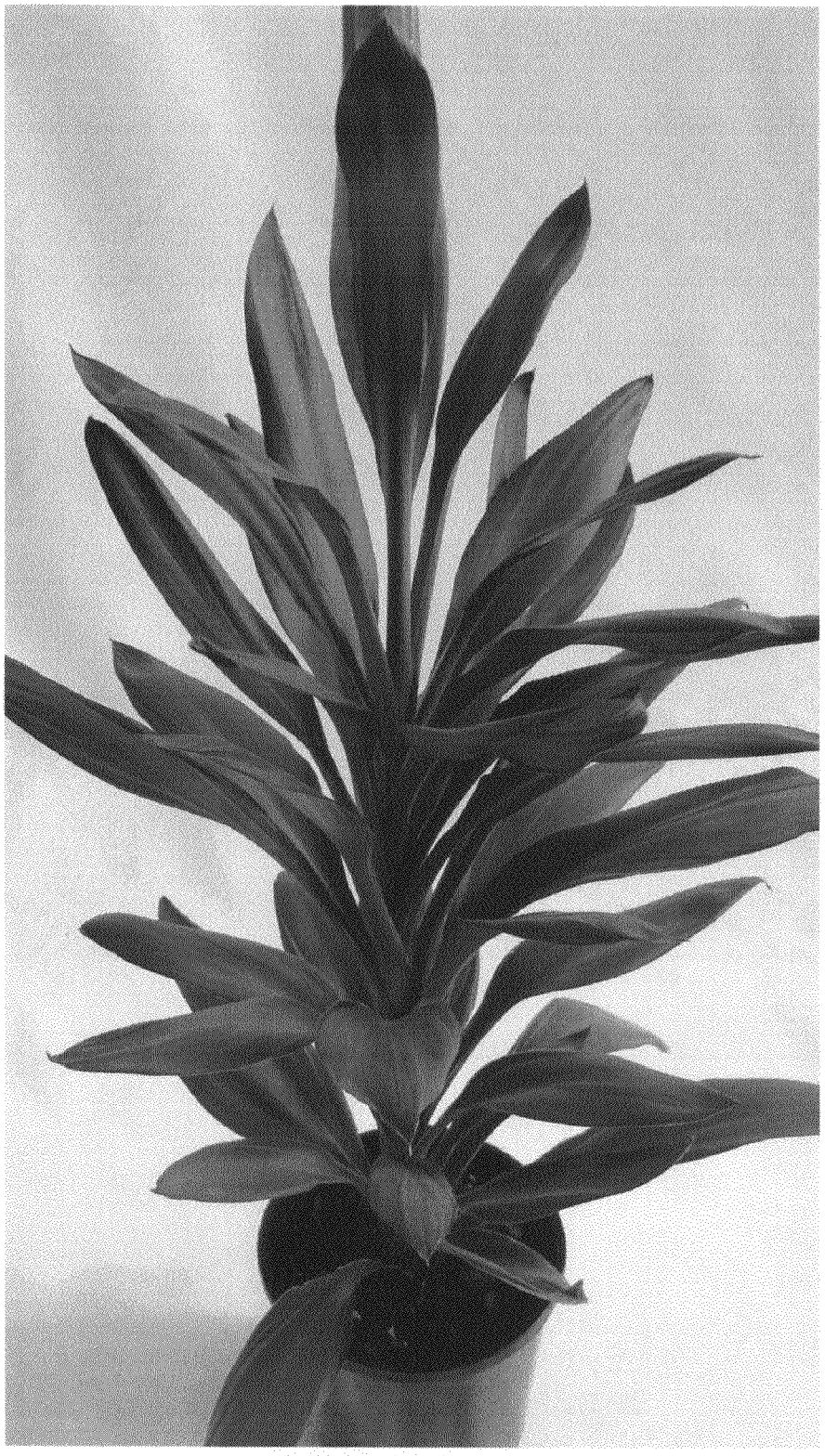

The accompanying photograph in FIG. 1 illustrates in full color a typical plant of 'Mystic Joy' grown under 50% shade cloth, in a 14 cm pot. This plant is approximately 7 weeks old from a rooted cutting.

Figure 2:
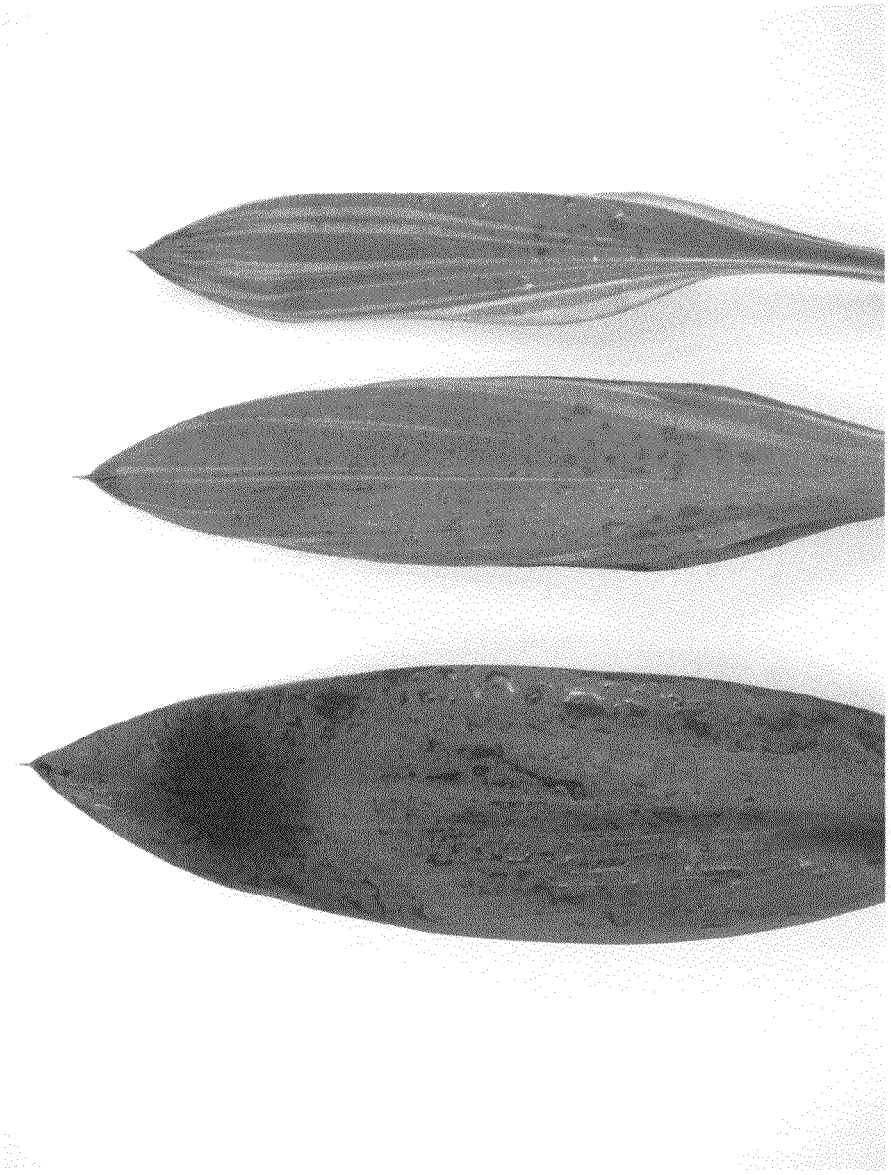

FIG. 2 illustrates a comparison of foliage of the new variety 'Mystic Joy' and the nearest comparator varieties, 'Glauca' and 'Pink Joy'. The leaf on the left is from *Cordyline brasiliensis* 'Glauca'. The center leaf is from a plant of 'Mystic Joy' and the leaf on the right is from a plant of 'Pink Joy'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'Mystic Joy' plants grown in under 50% shade in a shadehouse in Ninji, Queensland, Australia during Summer and Fall conditions. Temperatures ranged from 20° C. to 24° C. at night and 30° C. to 35° C. during the day. No pruning or chemical treatments were given. Measurements and numerical values represent averages of typical plant types.

Botanical classification: *Cordyline brasiliensis* 'Mystic Joy'.

PROPAGATION

Time to initiate rooting: Approximately 8 weeks, at around 15° C. soil temperature, 25° C. air.

Root description: Fine, fibrous.

PLANT

Age of plant described: Approximately 15 weeks.
Pot size of plant described: 14 cm.
Height: Approximately 20 cm.
Plant spread: Approximately 30 cm.
Growth rate: Vigorous, approximately 10 cm per month.
Growth of a 1 year old plant:
*Height*.—Approximately 100 cm.
*Plant spread*.—Approximately 50 cm.
Growth of a 2 year old plant:
*Height*.—Approximately 150 cm.
*Plant spread*.—Approximately 60 cm.
Branching characteristics: No branching.
Diameter of stem: Approximately 2.5 cm.
Length of stem: Approximately 20 cm.
Texture of stem: Glabrous.
Strength of stem: Very strong.
Color of stem: Near RHS Grey-Brown 199C.
Number of leaves per stem: Approximately 33.
Leaf:
*Arrangement*.—Whorled.
*Average length*.—Approximately 20 cm.
*Average width*.—Approximately 4.5 cm.
*Leaf internode length*.—Approximately 1 cm.
*Shape of blade*.—Lanceolate.
*Apex*.—Acuminate.
*Base*.—Attenuate.
*Margin*.—Entire.
*Attachment*.—Sheathing.
*Texture of top surface*.—Smooth, glabrous.
*Texture of bottom surface*.—Slightly rough.
*Color*.—Young foliage upper side: Near RHS Green 135D. Young foliage under side: Near RHS Green 139D with margin and faint striping near Purple 79D. Mature foliage upper side: Near RHS Greyed-Green 191B with Red-Purple 71B margin. Mature foliage under side: Near RHS Green 139D with margin and faint striping near Purple 79D.
Venation:
*Type*.—Parallel.
*Venation coloration*.—Upperside: Near RHS Greyed-Green 191B. Underside: Near RHS Green 139D.
Sheath:
*Average length*.—Approximately 6 cm.
*Average width*.—Approximately 1.7 cm.
*Color*.—Near RHS Greyed-Green 191B.
*Texture*.—Smooth, glabrous.

FLOWER

Not observed to date:

OTHER CHARACTERISTICS

Disease resistance: Mystic Joy shows a significantly better resistance to normal root rot diseases of *Cordyline brasiliensis* including Phythium, when compared to the similar variety, 'Pink Joy'.

Drought tolerance and cold tolerance: Hardy to 0° C., when grown under the protection of shade cloth. Tolerates temperatures up to at least 40° C.

Fruit/seed production: Not observed.

What is claimed is:

1. A new and distinct cultivar of *Cordyline* plant named 'Mystic Joy' as herein illustrated and described.

* * * * *